United States Patent
Xu et al.

(10) Patent No.: US 12,129,504 B2
(45) Date of Patent: Oct. 29, 2024

(54) CAPROATE-PRODUCING BACTERIUM WITH MULTIPLE SUBSTRATE UTILIZATION CAPABILITIES AND ITS APPLICATIONS

(71) Applicant: Jiangnan University, Wuxi (CN)

(72) Inventors: Yan Xu, Wuxi (CN); Cong Ren, Wuxi (CN); Huilin Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 18/373,435

(22) Filed: Sep. 27, 2023

(65) Prior Publication Data
US 2024/0102058 A1    Mar. 28, 2024

Related U.S. Application Data

(63) Continuation of application No. PCT/CN2022/084794, filed on Apr. 1, 2022.

(30) Foreign Application Priority Data

Apr. 6, 2021    (CN) .......................... 202110368762.7

(51) Int. Cl.
  *C12P 7/40*   (2006.01)
  *C12G 3/06*   (2006.01)
  *C12N 1/20*   (2006.01)

(52) U.S. Cl.
  CPC .................. *C12P 7/40* (2013.01); *C12G 3/06* (2013.01); *C12N 1/205* (2021.05)

(58) Field of Classification Search
  CPC ..... C12P 7/40; C12P 7/46; C12G 3/06; C12G 3/02; C12N 1/205; C12N 1/20; C12R 2001/01
  See application file for complete search history.

(56) References Cited

U.S. PATENT DOCUMENTS

2019/0091250 A1    3/2019    Bhaduri et al.

FOREIGN PATENT DOCUMENTS

| CN | 111778181 A |   | 10/2020 |          |
|----|-------------|---|---------|----------|
| CN | 112094746 A |   | 12/2020 |          |
| CN | 112458031 A |   | 3/2021  |          |
| CN | 113186121 A |   | 7/2021  |          |
| CN | 113322205 A | * | 8/2021  | C12N 1/20 |

OTHER PUBLICATIONS

Espacenet translation of Xu CN 113322205 A retrieved on Mar. 12, 2024 from https://worldwide.espacenet.com/patent/search/family/077419856/publication/CN113322205A?q=pn%3DCN113322205A (Year: 2024).*

Cong CN112458031 translation retrieved on Jun. 25, 2024 from https://worldwide.espacenet.com/patent/search/family/074803425/publication/CN112458031A?q=pn%3DCN112458031 (Year: 2024).*

He, Peixin et al. "Research and application progress of "ethyl caproate-increasing and ethyl lactate-decreasing" in brewing of Chinese Luzhou-flavor liquor" Journal of Light Industry. vol. 33 (4) Jul. 15, 2018.

Flaiz M et. al., "*Caproicibacter fermentans* gen. nov. sp. nov. a new caproate-producing bacterium and emended description of the genus *Caproiciproducens*", International Journal of Systematic and Evolutionary Microbiology, vol. 70 (7),Jul. 31, 2020.

* cited by examiner

Primary Examiner — Louise W Humphrey
Assistant Examiner — Kimberly Breen
(74) Attorney, Agent, or Firm — IPRO, PLLC (57) ABSTRACT

The disclosure discloses *Oscillospiraceae* sp. LBM10036 capable of utilizing multiple substrates and application thereof, and belongs to the fields of microbial technology and Baijiu brewing. The microorganism *Oscillospiraceae* sp. LBM10036 of the disclosure was preserved in the Guangdong Microbial Culture Collection Center on Sep. 21, 2020, with the preservation number GDMCC No. 61202. The *Oscillospiraceae* sp. LBM10036 of the disclosure has the capability to utilize diverse substrates and high product specificity, adapts to low pH, and can efficiently synthesize caproic acid under a pH of 5.0-5.5. The strain used in the disclosure can be used for strengthening microorganisms in pit mud, and improving the quality of degraded pit mud, to improve the quality of Strong aroma-type Baijiu, and also can be used for producing caproic acid from a variety of sugars and lactic acid by microbial fermentation.

9 Claims, 2 Drawing Sheets

Figure 4

CAPROATE-PRODUCING BACTERIUM WITH MULTIPLE SUBSTRATE UTILIZATION CAPABILITIES AND ITS APPLICATIONS

TECHNICAL FIELD

The disclosure relates to *Oscillospiraceae* sp. capable of utilizing multiple substrates and application thereof, and belongs to the fields of microbial technology and Baijiu brewing.

BACKGROUND

As the precursor of ethyl caproate, the main aroma component of strong aroma-type Baijiu, caproic acid is the most important medium chain fatty acid in strong aroma-type Baijiu. Meanwhile, caproic acid is also an important industrial product, and can be esterified with ethanol to produce ethyl caproate that can be used as a food additive to enhance the aroma of foods such as butter, cheese, and bread. As a natural antibacterial agent, caproic acid can improve animal gut microbiota and enhance animal immunity, thus being widely used in the animal breeding industry. With a high energy density, caproic acid is a valuable intermediate for chemicals or fuels, and can be used to produce biodiesel that can be used as aviation fuel. Caproic acid is also a precursor for synthesizing various pharmaceutical products. Therefore, caproic acid has broad industrial application prospects.

Caproic acid can be obtained by chemical synthesis or microbial fermentation. Due to the fact that microbial fermentation can use urban waste or industrial by-products as raw materials for the synthesis of caproic acid, which is in line with the principle of sustainable development, microbial fermentation is a promising anaerobic microbial fermentation technology. Caproate-producing bacteria are very important class of acid-producing microorganisms in the production of strong aroma-type Baijiu. Caproic acid produced by the metabolism of caproate-producing bacteria and alcohol produced by Daqu fermentation generate ethyl caproate, which is the key aroma compound of strong aroma-type liquor. Caproate-producing bacteria culture broth can be widely used in the production of strong aroma-type liquor for acid production strengthening, pit maintenance, artificial pit mud cultivation, esterified liquid production, etc., to improve and enhance the quality of strong aroma-type liquor.

At present, the main discovered caproic acid producing microorganisms include *Clostridium kluyveri, Caproiciproducens galactitolivorans* BS-1, *Ruminococcaceae bacterium* CPB6, *Caproicibacter fermentans* EA1, *Megasphaera hexanoica, Megasphaera elsdenii, Eubacterium pyruvativorans* and *Caproiciproducens* sp. JNLZ26 (disclosed in CN112458031A Chinese invention patent application).

*Ruminococcaceae bacterium* CPB6 is currently the strain with the highest yield of caproic acid reported. Under batch fed fermentation, *Ruminococcaceae bacterium* CPB6 can synthesize 16.6 g/L caproic acid utilizing 45.1 g/L lactic acid, with a maximum yield of 5.29 g/L/d (recorded in Chinese invention patent CN106834177B). However, *C. kluyveri* is the oldest and most comprehensively studied caproate-producing bacteria. However, the current strains capable of synthesizing caproic acid often have a narrow substrate spectrum, for example, *C. kluyveri* mainly utilizes ethanol as the substrate for synthesizing caproic acid; and the above CPB6 mainly utilizes lactic acid as the carbon source for high production of caproic acid. How to directly convert sugars widely present in nature, e.g., starch, glucose, and maltose, into caproic acid with high efficiency through one-step fermentation is an urgent technical problem in the biological synthesis of caproic acid.

caproate-producing bacteria is also one of important functional microorganisms in the brewing system of strong aroma-type Baijiu. The content and metabolic activity of caproate-producing bacteria in pit mud are closely related to the quality of strong aroma-type Baijiu. Caproate-producing bacteria is also a key strain resource for artificial aging of pit mud and strengthening of pit mud. Caproate-producing bacteria with excellent performance when used for pit mud cultivation can improve the quality of pit mud in a relatively short period of time and ultimately improve the quality of strong aroma-type Baijiu. The currently isolated caproate-producing bacteria from pit mud includes *Ruminococcaceae bacterium* CPB6, *Caproiciproducens* sp. JNLZ26, and *C. kluyveri*.

Therefore, caproate-producing bacteria that can tolerate low pH, grow vigorously, utilize diverse substrates, and have strong capability to produce caproic acid is of great significance for strengthening pit mud and production of caproic acid by microbial anaerobic fermentation.

CONTENTS OF THE INVENTION

Technical Problem

The technical problem to be solved by the present invention is to provide a caproic acid bacterium resistant to low pH, vigorous in growth, strong in producing caproic acid, and able to utilize various substrates.

Technical Solution

In order to solve the above technical problems, the disclosure provides an *Oscillospiraceae* sp., preserved in the Guangdong Microbial Culture Collection Center on Sep. 21, 2020, with the preservation number GDMCC No. 61202, at $5^{th}$ floor, Building 59, No. 100, Xianlie Middle Road, Guangzhou, Guangdong Institute of Microbiology.

The *Oscillospiraceae* sp. was screened from pit mud of a strong aroma-type Baijiu brewing system, and is capable of utilizing a variety of substrates to efficiently synthesize caproic acid from glucose, maltose, starch and lactic acid. The *Oscillospiraceae* sp. was isolated from the pit mud of the strong aroma-type Baijiu brewing system by utilizing a glucose-specific enrichment medium (modified *Clostridium* growth medium). After 16S rRNA gene sequencing, the strain was identified as a microorganism in the *Oscillospiraceae* family and named *Oscillospiraceae* sp. LBM10036.

The morphology of the *Oscillospiraceae* sp. on a modified solid *Clostridium* growth medium is: an opaque white circular colony with a smooth surface and neat edges. The *Oscillospiraceae* sp. is bluntly rounded at both ends and short rod-shaped in morphology under an electron microscope.

The disclosure further provides a microbial agent containing the *Oscillospiraceae* sp. LBM10036.

In one embodiment of the disclosure, the microbial agent is one or more liquid or solid microbial agents containing live cells of the *Oscillospiraceae* sp. LBM10036, freeze-dried cells of the *Oscillospiraceae* sp. LBM10036, and immobilized cells of the *Oscillospiraceae* sp. LBM10036.

In one embodiment of the disclosure, a preparation method of the liquid microbial agent includes: inoculating a sterilized liquid medium with an activated seed solution at an inoculum concentration of 2%-10% (w/w), and conducting cultivation at 35-37° C. for 24-72 h.

In one embodiment of the disclosure, the liquid medium is an modified *Clostridium* growth medium.

In one embodiment of the disclosure, a preparation method of the solid microbial agent includes: centrifuging the fermentation broth of the *Oscillospiraceae* sp. LBM10036 after fermentation to remove the medium, mixing the bacterial cells with a protective agent, pre-freezing the mixture at −80° C. for 2-4 h, and freeze-drying the mixture using a vacuum freeze-drying machine at a vacuum degree of 66.66 pa for 24-48 h.

In one embodiment of the disclosure, the protective agent is skimmed milk.

In one embodiment of the disclosure, the *Oscillospiraceae* sp. LBM10036 has an optimal pH of 5.0-5.5, can adapt to new and degraded pit mud environments with a lower pH, grows well at a low pH, and has a significant effect on strengthening pit mud with a low pH in practice.

The disclosure further provides applications of the aforementioned *Oscillospiraceae* sp. LBM10036, a bacterial suspension thereof, a culture solution thereof, a fermentation product thereof, or the aforementioned microbial agents in any of the following aspects a to d:
a. preparation of caproic acid and/or ethyl caproate;
b. preparation of products containing caproic acid and/or ethyl caproate;
c. strengthening of pit mud;
d. liquor brewing.

The disclosure further provides a method for producing caproic acid, and the caproic acid is produced by fermentation of the *Oscillospiraceae* sp. LBM10036.

In one embodiment of the disclosure, the *Oscillospiraceae* sp. utilizes one or more of glucose, fructose, maltose, starch, and lactic acid as carbon sources.

In one embodiment of the disclosure, the fermentation further includes utilizing acetate or butyrate as a cosubstrate.

In one embodiment of the disclosure, the fermentation is conducted at a temperature of 35-37° C. for 3-4 d, at an initial pH of fermentation of 5.5-6.5.

In one embodiment of the disclosure, the concentration of glucose is 10-40 g/L; the concentration of fructose is 10-40 g/L; the concentration of maltose is 10-40 g/L; the concentration of starch is 10-40 g/L; and the concentration of the lactic acid is 10-40 g/L.

In one embodiment of the disclosure, the method includes the following steps:
(1) inoculating an modified *Clostridium* growth medium with the *Oscillospiraceae* sp. LBM10036 for activation to prepare a primary seed solution;
(2) inoculating an modified *Clostridium* growth medium with the prepared seed solution, and conducting anaerobic cultivation at 35-37° C. for 18-30 h until the OD600 of the seed solution is 1.5-2.0 to obtain a secondary seed solution; and
(3) inoculating an modified *Clostridium* growth medium with the prepared secondary seed solution for fermentation to obtain caproic acid.

In one embodiment of the disclosure, the modified *Clostridium* growth medium and a preparation method thereof are as follows:

The medium contains (calculated in g/L): glucose 10.0-20.0, yeast extract 10.0, peptone 10.0, dipotassium hydrogen phosphate 1.0, potassium dihydrogen phosphate 0.5, ammonium sulfate 2.0, magnesium sulfate 0.1, and a cosubstrate 5.0, as well as a trace element nutrient solution 0.15-1.0 (mL/L). The cosubstrate is one or both of acetate and butyrate. The carbon source is one or two of glucose, maltose, starch, and lactic acid.

The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium is sterilized at 115° C. for 30 min.

In one embodiment of the disclosure, in step (1), the activation is conducted for at least 2 generations.

In one embodiment of the disclosure, in step (1), the activation is conducted at 35-37° C. for conducting anaerobic standing cultivation for 12-18 h until the $OD_{600}$ is 1.5-2.0.

In one embodiment of the disclosure, in step (2), the inoculum concentration of the seed solution is 5% (v/v).

In one embodiment of the disclosure, in step (3), the inoculum concentration of the culture solution is 5% (v/v).

In one embodiment of the disclosure, when glucose is utilized as the carbon source, in step (3), the fermentation medium is the same as the aforementioned modified *Clostridium* growth medium.

In one embodiment of the disclosure, when maltose is utilized as the carbon source, in step (3), as for the fermentation medium, the glucose in the modified *Clostridium* growth medium is replaced with maltose.

In one embodiment of the disclosure, when starch is utilized as the carbon source, in step (3), as for the fermentation medium, the glucose in the modified *Clostridium* growth medium is replaced with starch.

In one embodiment of the disclosure, when lactic acid is utilized as the carbon source, in step (3), as for the fermentation medium, the glucose in the modified *Clostridium* growth medium is replaced with lactic acid.

In one embodiment of the disclosure, when glucose and lactic acid are utilized as the carbon sources, in step (3), as for the fermentation medium, lactic acid is additionally added as the carbon source to the modified *Clostridium* growth medium.

In one embodiment of the disclosure, when glucose and lactic acid are utilized as carbon sources, the pH of the fermentation process is controlled by adjusting the ratio of carbon sources.

In one embodiment of the disclosure, when glucose and lactic acid are utilized as carbon sources, the application method of controlling the pH of a culture system by adjusting the ratio of carbon sources is to conduct batch fermentation utilizing the *Oscillospiraceae* sp. LBM10036, and inoculate a fermentation medium utilizing the glucose and the lactic acid as dual carbon sources with a strain. The required pH can be reached by adjusting the ratio of the glucose to the lactic acid. When the mass concentration ratio of the glucose to the lactic acid is greater than 1, the fermentation endpoint pH is slightly acidic, and when the mass concentration ratio of the glucose to the lactic acid is less than 1, the fermentation endpoint pH is slightly alkaline.

The disclosure further provides a method for producing strong aroma-type Baijiu, the fermentation is augmented by inoculating the aforementioned microbial agents of the aforementioned *Oscillospiraceae* sp. LBM10036 during the fermentation produces of Baijiu.

The disclosure further provides a method for strengthening of pit mud or rejuvenation of pit mud, the method is to inoculate a pit mud system to be strengthened with the forementioned liquid or solid microbial agent, in order to increase the number of *Oscillospiraceae* sp. in the pit mud, and improve the quality of Baijiu.

Beneficial Effects (1) The disclosure provides an *Oscillospiraceae* sp. LBM10036 strain screened from pit mud of a strong aroma-type Baijiu brewing system. The strain has an optimum pH of 5.0-5.5, and is tolerant to a brewing environment with a low pH. Because a fermentation system has a high lactic acid content and low pH, the *Oscillospiraceae* sp. LBM10036 tolerant to a lower pH is of significant application value.

(2) The *Oscillospiraceae* sp. LBM10036 provided by the disclosure can utilize a variety of substrates, e.g., glucose, maltose, starch, and lactic acid, for growth and rapid and efficient synthesis of caproic acid, and can be used in the field of production of caproic acid by anaerobic microbial fermentation. The prepared high-vitality bacterial cells can be used for strengthening and rejuvenating pit mud. The strategy of combined carbon sources can control changes in the pH during the fermentation process by adjusting the addition ratio of different substrates, takes into account both cell growth and caproic acid synthesis, reduces use of chemical reagents such as hydrochloric acid and sodium hydroxide, improves economic benefits, and simplifies the fermentation process.

Preservation of Biological Materials

An *Oscillospiraceae* sp. LBM10036, named *Oscillospiraceae* sp., was preserved in the Guangdong Microbial Culture Collection Center on Sep. 21, 2020, with the preservation number GDMCC No. 61202, at $5^{th}$ floor, Building 59, No. 100, Xianlie Middle Road, Guangzhou, Guangdong Institute of Microbiology.

DETAILED DESCRIPTION

The pit mud involved in the following examples is the pit mud from the old pits of Anhui and Sichuan Strong aroma-type Baijiu factories, which is used after being mixed evenly.

Detection Methods Involved in the Following Examples are as Follows:

A Method for Detecting the Contents of Caproic Acid, Butyric Acid, and Acetic Acid:

A gas chromatograph Agilent GC-7890B is used for determination. A sample treatment method includes: taking and centrifuging 1 mL of fermentation broth at 12000 r/min for 5 min, taking 200 μL of supernatant, adding 50 μL of an internal standard solution (12.5 g/L pivalic acid, pH 2.5), shaking and mixing the solutions well, and taking 200 μL of the mixture for detection. The chromatographic column is an Alltech Econo Cap-Wax chromatographic column (30 m×0.25 μM×0.25 μm). The gas chromatography conditions are as follows: the injection volume is 1 μL, the split ratio is 30:1, the injector temperature is 220° C., the detector temperature is 250° C., the air flow rate is 400 mL/min, the carrier gas flow rate is 2 mL/min, and the hydrogen flow rate is 40 mL/min.

A Method for Detecting the Contents Ethyl Caproate, Ethyl Acetate, and Ethyl Lactate:

A gas chromatograph Agilent GC-7890B is used for determination. A sample treatment method includes: taking and centrifuging 1 mL of distillate at 12000 r/min for 5 min, taking 200 μL of supernatant, adding 50 μL of an internal standard solution (12.5 g/L n-amyl acetate prepared with a 60% ethanol solution), shaking and mixing the solutions well, and taking 200 μL of the mixture for detection. The gas chromatography conditions are as follows: the chromatographic column is an Alltech Econo Cap-Wax chromatographic column (30 m×0.25 μm×0.25 μm), the injection volume is 1 μL, the split ratio is 37:1, the injector temperature is 250° C., the detector temperature is 250° C., the air flow rate is 400 mL/min, the carrier gas flow rate is 2 mL/min, and the hydrogen flow rate is 40 mL/min.

A Method for Detecting the Contents of Glucose, Maltose, and Lactic Acid:

A high-performance liquid chromatograph Agilent 1260 is used for determination. A sample treatment method includes: taking and centrifuging 1 mL of fermentation broth at 12000 r/min for 5 min, and then filtering the fermentation broth with a 0.22 μm membrane. The chromatographic column is Aminex HPX-87H (300×7.8 mm). The liquid chromatography conditions are: the injection volume is 10 μL, a column oven is at 60° C., the flow rate is 0.6 mL/min, and a differential detector is used.

The total sugar content is determined by a phenol-sulfuric acid method. The specific steps include: taking 2.0 mL of a sample to be tested, adding 1.0 mL of 6% phenol and 5.0 mL of concentrated sulfuric acid, shaking the solutions well, cooling the mixture at room temperature for 30 min, and measuring the optical density at 490 nm.

A Method for Calculating the Concentration of Free Caproic Acid in a Medium

The concentration of free caproic acid is calculated according to $\lg[A]/[HA]=pH-pKa$.

The pH of the medium is 5.5, the pKa of caproic acid is 4.86, A represents the ionic caproic acid content in the medium, HA represents the free caproic acid content in the medium, and the sum of A and HA represents the total caproic acid content in the medium.

Example 1: Obtainment of *Oscillospiraceae* sp. LBM10036

I. Isolation and Purification of *Oscillospiraceae* sp. LBM10036

Specific steps are as follows:

1. Enrichment Cultivation of Pit Mud 80 mL of an enrichment medium was inoculated with 3 g of pit mud and anaerobically cultivated at 37° C. for 4 d, and transferred to a fresh enrichment medium at an inoculum concentration of 5%-10% (v/v) after 4 d and anaerobically cultivated at 37° C. for 4 d. The enrichment step was repeated 3-4 times to obtain an enriched fermentation broth with a high abundance of *Oscillospiraceae* sp. The enrichment medium was an modified *Clostridium* growth medium.

The enrichment medium contains (calculated in g/L): glucose 20.0, yeast powder 10.0, peptone 10.0, dipotassium hydrogen phosphate 1.0, potassium dihydrogen phosphate 0.5, ammonium sulfate 2.0, magnesium sulfate 0.1, and a cosubstrate 5.0, as well as a trace element nutrient solution 0.15-1.0 (mL/L). The cosubstrate is one or both of acetate and butyrate.

The trace element nutrient solution contains (calculated in g/L): calcium chloride 10, cobalt chloride 10, zinc sulfate 10, manganese sulfate 10, and ferrous sulfate heptahydrate 15.

The pH of the medium is 5.5-6.0, and the medium was sterilized at 115° C. for 30 min.

2. Strain Isolation and Purification

The enriched fermentation broth of *Oscillospiraceae* sp. was diluted in gradients ($10^{-1}$, $10^{-2}$, $10^{-3}$). 100 μL of each of the gradient diluents was taken and spread on an modified *Clostridium* growth medium supplemented with 2% agar and anaerobically cultivated at 37° C. for 7 d, and a single colony was picked for fermentation. The content of caproic acid in the fermentation broth was detected utilizing gas chromatography. Finally, a strain with a high yield of caproic acid was selected and named LBM10036.

II. Identification and Preservation of *Oscillospiraceae* sp. LBM10036

1. Morphological identification: the morphology of the strain LBM10036 was observed, and the LBM10036 growing on an modified *Clostridium* growth medium supplemented with 2% agar showed the following morphology: an opaque white circular colony with a smooth surface and neat edges. The *Oscillospiraceae* sp. is bluntly rounded at both ends and short rod-shaped in morphology under an electron microscope. The strain LBM10036 was identified as a microorganism of the *Oscillospiraceae* family by 16s rRNA gene full-length sequencing.

2. Strain preservation

The strain LBM10036 was named *Oscillospiraceae* sp. LBM10036 and preserved in the Guangdong Microbial Culture Collection Center on Sep. 21, 2020, with the preservation number GDMCC No. 61202.

Example 2: Acid Resistance of *Oscillospiraceae* sp. LBM10036

The growth of the *Oscillospiraceae* sp. LBM10036 was tracked and measured by designing liquid mediums with different initial pH.

Specific steps are as follows:

1. Preparation of Mediums (1) The Used Medium is an Modified *Clostridium* Growth Medium.

The medium contains (calculated in g/L): glucose 20.0, yeast powder 10.0, peptone 10.0, dipotassium hydrogen phosphate 1.0, potassium dihydrogen phosphate 0.5, ammonium sulfate 2.0, magnesium sulfate 0.1, and a cosubstrate 5.0, as well as a trace element nutrient solution 0.15-1.0 (mL/L). The cosubstrate is one or both of acetate and butyrate. The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium was sterilized at 115° C. for 30 min.

(2) Preparation of Mediums with Different pH

The dissolved medium was divided into 9 blue cap bottles (100 mL), each blue cap bottle containing 100 mL of medium. Before sterilization, the pH of the mediums was adjusted to 3.5, 4.0, 4.5, 5.0, 5.5, 6.0, 6.5, 7.0, and 7.5 using hydrochloric acid (5 mol/L) or sodium hydroxide (5 mol/L), respectively. The mediums were sterilized at 115° C. for 30 min. After sterilization, the medium of each pH gradient was divided into 3 parts, each part containing 30 mL in a 50 mL centrifuge tube. The residual mediums were taken out of an anaerobic incubator and used for re-determining whether the actual pH met the experimental design.

2. Inoculation of the Mediums with Different pH with the *Oscillospiraceae* sp. LBM10036

(1) An *Oscillospiraceae* sp. LBM10036 frozen glycerol tube was taken out from a −80° C. refrigerator, activated for the first generation cultivation at 37° C. in the modified *Clostridium* growth medium described in step (1) until the OD600 was 1.5-2.0, and then transferred to a fresh modified *Clostridium* growth medium at an inoculum concentration of 5% (v/v) and activated for the second generation cultivation for 12-18 h until the OD600 was 1.5-2.0.

(2) After activation for two generations, 100 mL of the modified *Clostridium* growth medium described in step (1) was inoculated at an inoculum concentration of 5% (v/v) and cultivated until the GD value was 1.5-2.0, to prepare a seed solution.

Figure 1:
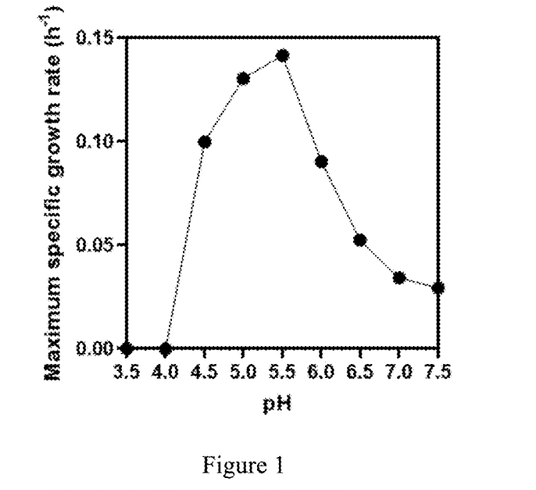
FIG. 1 shows the maximum specific growth rate of the *Oscillospiraceae* sp. LBM10036 at different pH.

(3) The mediums with different pH gradients prepared in step (2) were inoculated with the prepared seed solution at an inoculum concentration of 500 (v/v). The medium of each pH gradient had 3 replicates, and sampled from 0 to 96 h at an interval of 12 h. The OD600 was measured using a spectrophotometer, and the results are shown in Tables 1-2. The maximum specific growth rates under different pH gradients were plotted (as shown in FIG. 1).

TABLE 1

| OD600 values under different pH (1) | | | | | |
|---|---|---|---|---|---|
| Time | pH 3.5 | pH 4.0 | pH 4.5 | pH 5.0 | pH 5.5 |
| 0 h | 0.65 ± 0.23 | 0.59 ± 0.13 | 0.56 ± 0.06 | 0.46 ± 0.09 | 0.41 ± 0.03 |
| 12 h | 0.26 ± 0.01 | 0.29 ± 0.00 | 0.66 ± 0.03 | 1.20 ± 0.08 | 1.03 ± 0.06 |
| 24 h | 0.29 ± 0.01 | 0.35 ± 0.03 | 1.94 ± 0.08 | 2.92 ± 0.06 | 2.85 ± 0.09 |
| 48 h | 0.29 ± 0.02 | 0.34 ± 0.04 | 2.51 ± 0.00 | 3.20 ± 0.05 | 3.22 ± 0.23 |
| 72 h | 0.34 ± 0.02 | 0.37 ± 0.03 | 2.21 ± 0.29 | 2.95 ± 0.16 | 2.97 ± 0.05 |

TABLE 2

| OD600 values under different pH (2) | | | | |
|---|---|---|---|---|
| Time | pH 6.0 | pH 6.5 | pH 7.0 | pH 7.5 |
| 0 h | 0.41 ± 0.05 | 0.46 ± 0.07 | 0.45 ± 0.03 | 0.48 ± 0.03 |
| 12 h | 0.89 ± 0.01 | 0.78 ± 0.03 | 0.73 ± 0.04 | 0.61 ± 0.04 |
| 24 h | 2.18 ± 0.14 | 1.26 ± 0.08 | 0.92 ± 0.04 | 0.74 ± 0.04 |
| 48 h | 3.14 ± 0.00 | 2.48 ± 0.30 | 1.76 ± 0.10 | 1.23 ± 0.04 |
| 72 h | 3.33 ± 0.21 | 3.06 ± 0.03 | 2.63 ± 0.27 | 1.28 ± 0.03 |

The results show that, as shown in Tables 1-2 and FIG. 1, the *Oscillospiraceae* sp. LBM10036 grows at a pH of 4.5-7.5. The optimal pH for the growth of the *Oscillospiraceae* sp. LBM10036 is 5.0-5.5, which is slightly acidic. At a pH of 4.5, the maximum specific growth rate of the *Oscillospiraceae* sp. LBM10036 is 0.1 $h^{-1}$.

However, the research published in the Chinese patent application document CN108865942A shows that the optimal pH for *C. kluyveri* is 7.0, and at a pH of 4.5, the maximum specific growth rate of the *C. kluyveri* is about 0.01 h$^{-1}$.

The results indicate that the *Oscillospiraceae* sp. LBM10036 has superior capability to adapt to a low pH and has great application prospects.

3. Growth Conditions of the *Oscillospiraceae* sp. LBM10036 at Different Temperatures (1) An *Oscillospiraceae* sp. LBM10036 frozen glycerol tube was taken out from a −80° C. refrigerator, activated for the first generation cultivation at 37° C. in the modified *Clostridium* growth medium described in step (1) of step 1 until the OD600 was 1.5-2.0, and then transferred to a fresh modified *Clostridium* growth medium at an inoculum concentration of 5% (v/v) and activated for the second generation cultivation for 12-18 h until the OD600 was 1.5-2.0.

(2) After activation for two generations, 100 mL of the modified *Clostridium* growth medium described in step (1) was inoculated at an inoculum concentration of 5% (v/v) and cultivated until the OD value was 1.5-2.0, to prepare a seed solution.

(3) The modified *Clostridium* growth medium was inoculated with the prepared seed solution at an inoculum concentration of 5% (v/v), and cultivated at 20° C., 25° C., 30° C., 35° C., 40° C., and 45° C. for 48 h, respectively. The OD600 was measured using a spectrophotometer, and the results are shown in Table 3:

TABLE 3

OD600 values under different temperatures

| Time | 20° C. | 25° C. | 30° C. | 35° C. | 40° C. | 45° C. |
|---|---|---|---|---|---|---|
| 0 h | 0.30 ± 0.01 | 0.32 ± 0.02 | 0.32 ± 0.03 | 0.34 ± 0.00 | 0.29 ± 0.02 | 0.30 ± 0.02 |
| 48 h | 0.42 ± 0.02 | 0.50 ± 0.10 | 2.13 ± 0.13 | 2.97 ± 0.15 | 2.27 ± 0.07 | 0.25 ± 0.02 |

The results show that the optimal temperature for the growth of the *Oscillospiraceae* sp. LBM10036 is 30-40° C.

Example 3: Synthesis of Caproic Acid with the *Oscillospiraceae* sp. LBM10036 Utilizing Glucose as a Carbon Source and Sodium Acetate as a Cosubstrate Specific steps are as follows:
1. Preparation of a Medium The medium contains (calculated in g/L): glucose 15.0, yeast powder 10.0, peptone 10.0, dipotassium hydrogen phosphate 1.0, potassium dihydrogen phosphate 0.5, ammonium sulfate 2.0, magnesium sulfate 0.1, and sodium acetate 5.0, as well as a trace element nutrient solution 0.15-1.0 (mL/L).

The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium was sterilized at 115° C. for 30 min.

2. Synthesis of Caproic Acid

The medium prepared in step 1 was inoculated with the *Oscillospiraceae* sp. LBM10036 preserved at −80° C. and was cultivated at 37° C. until the OD600 was 1.5-2.0, and then transferred to a fresh medium prepared in step 1 at an inoculum concentration of 5% (v/v) and cultivated for 12-18 h to obtain a primary seed solution.

100 mL of the medium prepared in step 1 was inoculated with the prepared primary seed solution at an inoculum concentration of 5% (v/v) and anaerobically cultivated at 37° C. for 12-18 h until the OD600 was 1.5-2.0 to obtain a secondary seed solution.

The prepared secondary seed solution was transferred into 100 mL of the medium prepared in step 1 at an inoculum concentration of 5% (v/v) for conducting anaerobic standing fermentation at 37° C. for 72 h.

3 replicates were set and sampled from 0 to 72 h at an interval of 12 h. The OD600 was measured using a spectrophotometer, the pH of the fermentation broth was measured using a pH meter, the contents of caproic acid, butyric acid, and acetic acid in the fermentation supernatant were determined by gas chromatography, and the glucose content was determined by liquid chromatography. The specific results are shown in Table 4.

TABLE 4

Growth, substrate utilization and metabolite production of the strain LBM10036 utilizing glucose as the carbon source

| Time | OD600 | pH | Glucose (g/L) | Acetic acid (g/L) | Butyric acid (g/L) | Caproic acid (g/L) |
|---|---|---|---|---|---|---|
| 0 h | 0.30 ± 0.03 | 5.91 ± 0.09 | 15.66 ± 2.90 | 2.73 ± 1.17 | 0.00 ± 0.00 | 0.00 ± 0.00 |
| 12 h | 0.87 ± 0.57 | 5.62 ± 0.10 | 13.63 ± 1.67 | 2.03 ± 0.19 | 0.21 ± 0.04 | 0.57 ± 0.11 |
| 24 h | 2.45 ± 0.64 | 5.45 ± 0.11 | 9.91 ± 3.32 | 2.06 ± 0.55 | 0.72 ± 0.12 | 1.96 ± 0.31 |
| 48 h | 3.43 ± 0.28 | 5.24 ± 0.08 | 5.70 ± 2.41 | 1.23 ± 0.35 | 0.93 ± 0.11 | 3.91 ± 0.35 |
| 72 h | 2.85 ± 0.43 | 5.19 ± 0.06 | 4.67 ± 1.44 | 1.18 ± 0.19 | 0.93 ± 0.08 | 4.26 ± 0.39 |

As shown by the experimental results in Table 4, the synthesis of caproic acid is coupled with the growth of the *Oscillospiraceae* sp. LBM10036. Utilizing glucose (15 g/L) as the carbon source and without controlling the pH, the yield of caproic acid produced by the *Oscillospiraceae* sp. LBM10036 utilizing the glucose (10 g/L) is 4.26 g/L, and the production efficiency is 1.42 g/L/d obtained by dividing the yield of the caproic acid (4.26 g/L) on the 72$^{nd}$ h (day three) by the number of days (3) of fermentation.

The *Oscillospiraceae* sp. LBM10036 reaches the maximum biomass at 48 h, with an OD600 of 3.43. The *C. kluyveri* reaches the maximum biomass by fermentation for 192 h without pH control, with an OD600 of 0.36, therefore, when glucose is utilized as the carbon source and sodium acetate is utilized as the cosubstrate, the maximum biomass of the *Oscillospiraceae* sp. LBM10036 is 9.5 times that of the *C. kluyveri*.

Example 4: Synthesis of Caproic Acid with the *Oscillospiraceae* sp. LBM10036 Utilizing Maltose as a Carbon Source and Sodium Acetate as a Cosubstrate Specific steps are as follows:
1. Preparation of a Medium The medium contains (calculated in g/L): maltose 36.0, yeast powder 10.0, peptone 10.0, dipotassium hydrogen phosphate 1.0, potassium dihydrogen phosphate 0.5, ammonium sulfate 2.0, magnesium sulfate 0.1, and sodium acetate 5.0, as well as a trace element nutrient solution 0.15-1.0 (mL/L).

The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium was sterilized at 115° C. for 30 min.

2. Synthesis of Caproic Acid

The medium prepared in step 1 was inoculated with the *Oscillospiraceae* sp.

LBM10036 preserved at −80° C. and was activated for cultivation at 37° C. until the OD600 was 1.5-2.0, and then transferred to a fresh medium prepared in step 1 at an inoculum concentration of 5% (v/v) and cultivated for 12-18 h to obtain a primary seed solution.

100 mL of the medium prepared in step 1 was inoculated with the prepared primary seed solution at an inoculum concentration of 5% (v/v) and cultivated for 12-18 h until the OD600 was 1.5-2.0 to obtain a secondary seed solution.

The prepared secondary seed solution was transferred into 100 mL of the medium prepared in step 1 at an inoculum concentration of 5% (v/v) and anaerobically fermentated at 37° C.

3 replicates were set and sampled from 0 to 72 h at an interval of 12 h. The OD600 was measured using a spectrophotometer, the contents of caproic acid, butyric acid, and acetic acid in the fermentation supernatant were determined by gas chromatography, and the maltose content was determined by liquid chromatography. The specific results are shown in Table 5.

Specific steps are as follows:

1. Preparation of a Medium

The medium contains (calculated in g/L): starch 40.0, yeast powder 10.0, peptone 10.0, dipotassium hydrogen phosphate 1.0, potassium dihydrogen phosphate 0.5, ammonium sulfate 2.0, magnesium sulfate 0.1, and sodium acetate 5.0, as well as a trace element nutrient solution 0.15-1.0 (mL/L).

The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium was sterilized at 115° C. for 30 min.

2. Capability of *Oscillospiraceae* sp. LBM10036 to Synthesize Caproic Acid

The medium prepared in step 1 was inoculated with the *Oscillospiraceae* sp. LBM10036 preserved at −80° C. and was activated for cultivation at 37° C. until the OD600 was 2.0 to obtain a fermentation broth.

Figure 2:
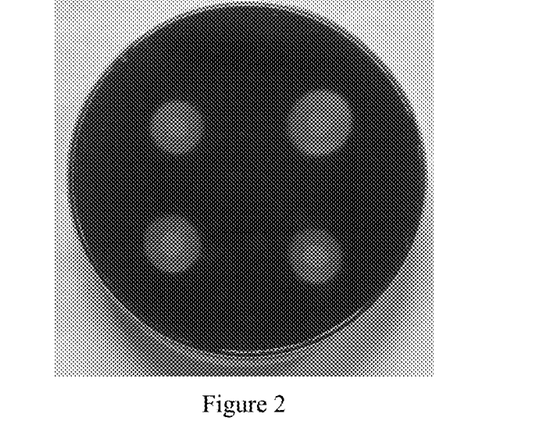
FIG. 2 shows that the *Oscillospiraceae* sp. LBM10036 forms a transparent circle around the colony after growing on a starch plate and being stained with an iodine solution.

1 μL of the fermentation broth with an OD600 of 2.0 was dropped to the medium prepared in step 1 with 2% agar added, and anaerobically cultivated at 37° C. for 96 h. Then the Lugol's iodine solution was used for staining and transparent circles were observed. After staining with the Lugol's iodine solution, as shown in FIG. 2, clear transparent circles appeared around the colonies, indicating that the *Oscillospiraceae* sp. LBM10036 is capable of utilizing starch.

TABLE 5

Substrate utilization and metabolite production of the strain LBM10036 utilizing maltose as the carbon source

| Time | OD600 | Maltose (g/L) | Acetic acid (g/L) | Butyric acid (g/L) | Caproic acid (g/L) |
| --- | --- | --- | --- | --- | --- |
| 0 h | 0.42 ± 0.05 | 36.50 ± 3.69 | 3.08 ± 0.44 | 0.00 ± 0.00 | 0.00 ± 0.00 |
| 12 h | 0.77 ± 0.04 | 33.54 ± 0.25 | 2.97 ± 0.19 | 0.13 ± 0.03 | 0.18 ± 0.06 |
| 24 h | 0.99 ± 0.05 | 31.75 ± 0.89 | 2.99 ± 0.35 | 0.31 ± 0.06 | 0.59 ± 0.14 |
| 48 h | 2.29 ± 0.21 | 25.16 ± 2.96 | 2.75 ± 0.09 | 0.92 ± 0.06 | 2.65 ± 0.24 |
| 72 h | 3.00 ± 0.20 | 24.33 ± 0.27 | 2.40 ± 0.05 | 1.07 ± 0.04 | 3.98 ± 0.25 |

As shown by the experimental results in Table 5, utilizing maltose (36 g/L) as the carbon source and without controlling the pH, the yield of caproic acid produced by the *Oscillospiraceae* sp. LBM10036 utilizing the maltose (12 g/L) is 3.98 g/L, and the production efficiency is 1.32 g/L/d obtained by dividing the yield of the caproic acid (3.98 g/L) on the $72^{nd}$ h (day three) by the number of days (3) of fermentation.

Example 5: Synthesis of Caproic Acid with the *Oscillospiraceae* sp. LBM10036 Utilizing Starch as a Carbon Source and Sodium Acetate as a Cosubstrate Starch is one of the most widely sourced biomass raw materials in nature and an important raw material for the production of many industrial products such as bioethanol and biobutanol. At present, ethanol is the main raw material for synthesizing caproic acid through microbial fermentation. There are no reported strains in nature capable of synthesizing caproic acid by degrading starch. This example demonstrates that the *Oscillospiraceae* sp. LBM10036 is capable of directly synthesizing caproic acid from starch, further improving the practical application value of the *Oscillospiraceae* sp. LBM10036.

3. Synthesis of Caproic Acid

The medium prepared in step 1 was inoculated with the *Oscillospiraceae* sp. LBM10036 preserved at −80° C. and was activated for cultivation at 37° C. until the OD600 was 1.5-2.0, and then transferred to a fresh medium prepared in step 1 at an inoculum concentration of 5% (v/v) and cultivated for 12-18 h to obtain a primary seed solution.

100 mL of the medium prepared in step 1 was inoculated with the prepared primary seed solution at an inoculum concentration of 5% (v/v) and anaerobically cultivated at 37° C. for 12-18 h until the OD600 was 1.5-2.0 to obtain a secondary seed solution.

The prepared secondary seed solution was transferred into 100 mL of the medium prepared in step 1 at an inoculum concentration of 5% (v/v) and anaerobically fermented at 37° C. for 72 h.

Three replicates were set for the fermentation experiment and sampled from 0 to 72 h at an interval of 12 h. The OD600 was measured using a spectrophotometer. The contents of caproic acid, butyric acid, and acetic acid in the fermentation supernatant were determined by gas chromatography, and the starch content was determined by a phenol-sulfuric acid method. The specific results are shown in Table 6.

TABLE 6

Substrate utilization and metabolite production of the strain LBM10036 utilizing starch as the carbon source

| Time | OD600 | Starch (g/L) | Acetic acid (g/L) | Butyric acid (g/L) | Caproic acid (g/L) |
|---|---|---|---|---|---|
| 0 h  | 0.21 ± 0.01 | 40.42 ± 4.40  | 2.52 ± 0.14 | 0.00 ± 0.00 | 0.00 ± 0.00 |
| 12 h | 0.55 ± 0.09 | 37.24 ± 5.15  | 2.33 ± 0.19 | 0.01 ± 0.01 | 0.06 ± 0.05 |
| 24 h | 1.32 ± 0.24 | 32.69 ± 7.24  | 2.43 ± 0.25 | 0.30 ± 0.03 | 0.78 ± 0.15 |
| 48 h | 2.39 ± 0.20 | 25.24 ± 12.11 | 1.82 ± 0.18 | 0.81 ± 0.02 | 2.43 ± 0.14 |
| 72 h | 2.08 ± 0.35 | 28.82 ± 2.97  | 1.51 ± 0.14 | 0.99 ± 0.06 | 3.39 ± 0.47 |

As shown by the results in Table 6, without controlling the pH, the yield of caproic acid produced by the *Oscillospiraceae* sp. LBM10036 utilizing starch (12 g/L) is 3.39 g/L, and the production efficiency is 1.13 g/L/d obtained by dividing the yield of the caproic acid (3.39 g/L) on the $72^{nd}$ h (day three) by the number of days (3) of fermentation.

Example 6: Synthesis of Caproic Acid with the *Oscillospiraceae* sp. LBM10036 Utilizing Lactic Acid as a Carbon Source and Sodium Acetate as a Cosubstrate Specific steps are as follows:
1. Preparation of a Medium The medium contains (calculated in g/L): lactic acid 15.0, yeast powder 10.0, peptone 10.0, dipotassium hydrogen phosphate 1.0, potassium dihydrogen phosphate 0.5, ammonium sulfate 2.0, magnesium sulfate 0.1, and sodium acetate 5.0, as well as a trace element nutrient solution 0.15-1.0 (mL/L).

The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium was sterilized at 115° C. for 30 min.

2. Synthesis of Caproic Acid

The medium prepared in step 1 was inoculated with the *Oscillospiraceae* sp. LBM10036 preserved at −80° C. and was activated for cultivation at 37° C. until the OD600 was 1.5-2.0, and then transferred to a fresh medium prepared in step 1 at an inoculum concentration of 5% (v/v) and cultivated for 12-18 h to obtain a primary seed solution.

100 mL of the medium prepared in step 1 was inoculated with the prepared primary seed solution at an inoculum concentration of 5% (v/v) and anaerobically cultivated at 37° C. for 12-18 h until the OD600 was 1.5-2.0 to obtain a secondary seed solution.

The prepared secondary seed solution was transferred into 100 mL of the medium prepared in step 1 at an inoculum concentration of 5% (v/v) and anaerobically fermented at 37° C. for 72 h.

3 replicates were set and sampled from 0 to 72 h at an interval of 12 h. The OD600 was measured using a spectrophotometer. The pH of the fermentation broth was measured using a pH meter, the contents of caproic acid, butyric acid, and acetic acid in the fermentation supernatant were determined by gas chromatography, and the lactic acid content was determined by liquid chromatography. The specific results are shown in Table 7.

TABLE 7

Substrate utilization and metabolite production of the strain LBM10036 utilizing lactic acid as the carbon source

| Time | OD600 | pH | Lactic acid (g/L) | Acetic acid (g/L) | Butyric acid (g/L) | Caproic acid (g/L) |
|---|---|---|---|---|---|---|
| 0 h  | 0.15 ± 0.01 | 6.25 ± 0.02 | 15.02 ± 0.02 | 2.09 ± 0.49 | 0.00 ± 0.00 | 0.24 ± 0.15 |
| 12 h | 0.32 ± 0.09 | 6.51 ± 0.02 | 14.37 ± 0.52 | 2.52 ± 0.14 | 0.08 ± 0.06 | 0.89 ± 0.20 |
| 24 h | 0.73 ± 0.09 | 7.16 ± 0.04 | 8.96 ± 0.70  | 2.04 ± 0.23 | 0.33 ± 0.05 | 3.81 ± 0.49 |
| 48 h | 0.73 ± 0.07 | 7.96 ± 0.15 | 1.10 ± 0.43  | 0.92 ± 0.46 | 0.49 ± 0.11 | 8.13 ± 0.46 |
| 72 h | 0.75 ± 0.06 | 8.04 ± 0.14 | 0.50 ± 0.00  | 0.83 ± 0.18 | 0.71 ± 0.07 | 7.69 ± 1.02 |

As shown by the experimental results in Table 7, utilizing lactic acid (15 g/L) as the carbon source and without controlling the pH, the *Oscillospiraceae* sp. LBM10036 reaches the maximum biomass at 72 h, with an OD600 of 0.75 and a maximum specific growth rate of 0.055 $h^{-1}$. The yield of caproic acid produced by the *Oscillospiraceae* sp. LBM10036 is about 8 g/L, and the production efficiency is 2.56 g/L/d obtained by dividing the yield of the caproic acid (7.69 g/L) on the $72^{nd}$ h (day three) by the number of days (3) of fermentation.

Example 7: Synthesis of Caproic Acid with the *Oscillospiraceae* sp. LBM10036 Utilizing Glucose and Lactic Acid as Double Carbon Sources Specific steps are as follows:
1. Preparation of a Medium The medium contains (calculated in g/L): glucose 3.5, lactic acid 7.0 (or, glucose 12.0, lactic acid 8.0), yeast powder 10.0, peptone 10.0, dipotassium hydrogen phosphate 1.0, potassium dihydrogen phosphate 0.5, ammonium sulfate 2.0, magnesium sulfate 0.1, and a cosubstrate 5.0, as well as a trace element nutrient solution 0.15-1.0 (mL/L). The cosubstrate is one or both of acetate and butyrate.

The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium was sterilized at 115° C. for 30 min.

2. Synthesis of Caproic Acid

The medium prepared in step 1 was inoculated with the *Oscillospiraceae* sp. LBM10036 (synthesized by caproic acid) preserved at −80° C. and was activated for cultivation at 37° C. until the OD600 was 1.5-2.0, and then transferred to a fresh medium prepared in step 1 at an inoculum concentration of 5% (v/v) and cultivated for 12-18 h to obtain a primary seed solution.

100 mL of the medium prepared in step 1 was inoculated with the prepared seed solution at an inoculum concentration of 5% (v/v) and anaerobically cultivated at 37° C. for 12-18 h until the OD600 was 1.5-2.0 to obtain a secondary seed solution.

The prepared secondary seed solution was transferred into 100 mL of an modified *Clostridium* growth medium utilizing lactic acid and glucose as carbon sources at an inoculum concentration of 5% (v/v) for conducting anaerobic fermentation at 37° C. for 96 h.

3 replicates were set and sampled from 0 to 96 h at an interval of 12 h. The OD600 was measured using a spectrophotometer. The pH of the fermentation broth was measured using a pH meter. The contents of caproic acid, butyric acid, and acetic acid in the fermentation supernatant were determined by gas chromatography, and the contents of glucose and lactic acid were determined by liquid chromatography. The specific results are shown in Tables 8-9.

Since the pH of the medium decreases when glucose is utilized for synthesizing caproic acid, and the pH of the medium increases when lactic acid is utilized for synthesizing caproic acid, the *Oscillospiraceae* sp. LBM10036 can simultaneously utilize lactic acid and glucose when the two carbon sources are utilized.

Therefore, when an appropriate ratio of carbon sources is adopted, the pH of the medium can be maintained stable and not rapidly decrease or increase to a value that inhibits the growth of the strains, thereby promoting full utilization of the substrate and improving the utilization efficiency of the substrate.

The fact that the *Oscillospiraceae* sp. LBM10036 synchronously utilizes lactic acid and glucose can also serve as a strategy for controlling the pH of a cultivation system when a fermentation tank is used. By adjusting the feeding of substrates in different ratios, the pH of the system can be controlled, thereby increasing the yield of caproic acid,

TABLE 8

Growth, substrate utilization, and metabolite production of the strain LBM10036, and changes in the pH of the medium utilizing glucose (3.5 g/L) and lactic acid (7 g/L) as the carbon sources

| Time | OD600 | pH | Glucose (g/L) | Lactic acid (g/L) | Acetic acid (g/L) | Butyric acid (g/L) | Caproic acid (g/L) |
|---|---|---|---|---|---|---|---|
| 0 h  | 0.17 ± 0.0  | 6.63 ± 0.04 | 3.26 ± 0.71 | 7.77 ± 1.65 | 2.06 ± 0.23 | 0.00 ± 0.00 | 0.18 ± 0.05 |
| 12 h | 0.24 ± 0.03 | 6.85 ± 0.03 | 3.09 ± 0.91 | 6.80 ± 1.51 | 1.84 ± 0.32 | 0.00 ± 0.00 | 0.30 ± 0.17 |
| 24 h | 0.48 ± 0.04 | 6.93 ± 0.04 | 3.52 ± 0.32 | 7.16 ± 0.19 | 2.20 ± 0.06 | 0.08 ± 0.02 | 1.25 ± 0.08 |
| 48 h | 1.24 ± 0.04 | 7.15 ± 0.08 | 0.25 ± 0.22 | 2.13 ± 0.16 | 1.81 ± 0.11 | 0.57 ± 0.06 | 4.25 ± 0.66 |
| 72 h | 0.78 ± 0.09 | 7.30 ± 0.11 | 0.00 ± 0.00 | 0.00 ± 0.00 | 1.93 ± 0.06 | 1.01 ± 0.05 | 5.64 ± 0.36 |
| 96 h | 0.76 ± 0.05 | 7.50 ± 0.02 | 0.00 ± 0.00 | 0.00 ± 0.00 | 2.12 ± 0.04 | 1.17 ± 0.04 | 5.73 ± 0.63 |

TABLE 9

Growth, substrate utilization, and metabolite production of the strain LBM10036, and changes in the pH of the medium utilizing glucose (12 g/L) and lactic acid (8 g/L) as the carbon sources

| Time | OD600 | pH | Glucose (g/L) | Lactic acid (g/L) | Acetic acid (g/L) | Butyric acid (g/L) | Caproic acid (g/L) |
|---|---|---|---|---|---|---|---|
| 0 h  | 0.12 ± 0.04 | 6.62 ± 0.03 | 12.72 ± 0.89 | 8.04 ± 0.62 | 2.85 ± 0.20 | 0.00 ± 0.00 | 0.21 ± 0.05 |
| 12 h | 0.23 ± 0.04 | 6.90 ± 0.04 | 12.16 ± 1.32 | 6.89 ± 1.05 | 2.35 ± 0.25 | 0.00 ± 0.01 | 0.54 ± 0.11 |
| 24 h | 0.44 ± 0.04 | 7.01 ± 0.10 | 11.63 ± 1.99 | 6.07 ± 1.14 | 2.16 ± 0.31 | 0.06 ± 0.02 | 0.89 ± 0.05 |
| 48 h | 0.91 ± 0.02 | 7.07 ± 0.05 | 10.38 ± 1.58 | 2.57 ± 0.28 | 1.89 ± 0.09 | 0.41 ± 0.04 | 3.78 ± 0.15 |
| 72 h | 1.74 ± 0.02 | 6.51 ± 0.03 | 5.26 ± 1.41  | 0.00 ± 0.00 | 1.82 ± 0.04 | 0.70 ± 0.01 | 9.63 ± 0.48 |
| 96 h | 2.02 ± 0.41 | 5.65 ± 0.09 | 0.30 ± 0.51  | 0.00 ± 0.00 | 2.23 ± 0.03 | 0.90 ± 0.02 | 11.36 ± 1.24 |

As shown in Table 8, when glucose (3.5 g/L) and lactic acid (7 g/L) are utilized as the carbon sources, i.e., the ratio of the glucose to the lactic acid is 1:2, the yield of caproic acid is 5.73 g/L and the production efficiency is 1.43 g/L/d after the strain LBM10036 is fermented for 96 h. The pH during the fermentation process gradually increases from 6.6 to 7.5, which is within the pH range without inhibiting the *Oscillospiraceae* sp. LBM10036, and the substrate is completely utilized.

As shown in Table 9, when glucose (12 g/L) and lactic acid (8 g/L) are utilized as the carbon sources, i.e., the ratio of the glucose to the lactic acid is 3:2, the yield of caproic acid is 11.36 g/L and the production efficiency is 2.84 g/L/d after the *Oscillospiraceae* sp. LBM10036 was fermented for 96 h. The pH during the fermentation process gradually increases from 6.6 to 7.0, and then decreases to 5.7, which is within the pH range without inhibiting the *Oscillospiraceae* sp. LBM10036, and the substrate is completely utilized.

avoiding use of chemicals such as hydrochloric acid and sodium hydroxide or ammonia, and making the fermentation process greener and safer.

Regardless of the ratio of carbon sources, the *Oscillospiraceae* sp. LBM10036 can simultaneously utilize lactic acid and glucose, without a preference for prioritizing use of a certain carbon source. Therefore, the *Oscillospiraceae* sp. LBM10036 can efficiently treat raw materials containing complex carbon sources, and has great practical application potential.

Example 8: Method for Preparing an *Oscillospiraceae* sp. LBM10036 Microbial Agent Due to the fact that the *Oscillospiraceae* sp. LBM10036 can obtain a higher biomass utilizing glucose as the carbon source, which is 2.8 times that of lactic acid as a carbon source, glucose was utilized as the carbon source for cultivating *Oscillospiraceae* sp. LBM10036 cells to prepare a microbial agent. Considering that addition of cosubstrates can promote synthesis of caproic acid in the strain, and high concentrations of caproic acid have a toxic effect on the strain and inhibit strain growth, no cosubstrates such as acetate or butyrate were added to the medium when the microbial agent was prepared.

1. Preparation of a Medium

The medium is a modified *Clostridium* growth medium without any cosubstrate, and contains (calculated in g/L): glucose 20.0, yeast powder 10.0, peptone 10.0, dipotassium hydrogen phosphate 1.0, potassium dihydrogen phosphate 0.5, ammonium sulfate 2.0, and magnesium sulfate 0.1, as well as a trace element nutrient solution 0.15-1.0 (mL/L). The trace element nutrient solution contains (calculated in g/L): calcium chloride 10, cobalt chloride 10, zinc sulfate 10, manganese sulfate 10, and ferrous sulfate heptahydrate 15. The pH of the medium was adjusted to 5.5 utilizing the hydrochloric acid (5 mol/L), and the medium was sterilized at 115° C. for 30 min.

2. Inoculation with the *Oscillospiraceae* sp. LBM10036

The medium prepared in step 1 was inoculated with the *Oscillospiraceae* sp. LBM10036 (synthesized by caproic acid) preserved at −80° C. and was activated for cultivation at 37° C. until the OD600 was 1.5-2.0, and then transferred to a fresh medium prepared in step 1 at an inoculum concentration of 5% (v/v) and cultivated for 12-18 h to obtain a primary seed solution.

One hundred mL of the medium prepared in step 1 was inoculated with the prepared seed solution at an inoculum concentration of 5% (v/v) and cultivated for 12-18 h until the OD600 was 1.5-2.0 to obtain a secondary seed solution.

Figure 3:
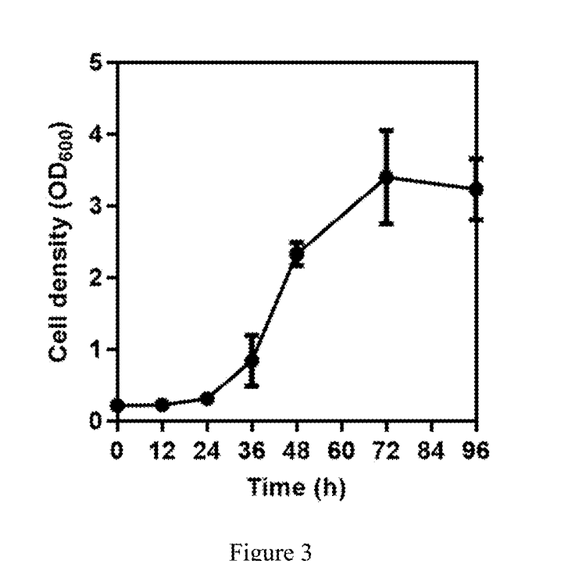
FIG. 3 shows a growth curve of the *Oscillospiraceae* sp. LBM10036 utilizing glucose as a carbon source without any cosubstrate.

The prepared secondary seed solution was transferred into 1 L of the medium prepared in step 1 at an inoculum concentration of 5% (v/v) and fermented. After fermentation at 37° C. for 72-96 h, bacterial cells were collected by centrifugation, and a bacterial growth curve is shown in FIG. 3.

3. Preparation of a Solid Microbial Agent

The bacterial cells and a protective agent (skimmed milk) were uniformly mixed in a ratio of 5:1 (5 mL of fermentation broth corresponds to 1 mL of protective agent), contained in glass petri dishes with each petri dish containing 20 mL, sealed with a cling film, pre-frozen at −80° C. for 2-4 h, and freeze-dried using a vacuum freeze drier under a vacuum degree of 66.66 pa for 24-48 h, to obtain the solid microbial agent containing the *Oscillospiraceae* sp. LBM1036.

Example 9: Fermentation of Strong Aroma-Type Baijiu without Pit Mud Utilizing *Oscillospiraceae* sp. LBM10036

Specific steps are as follows:

(1) Preparation of a Medium

The medium contains (calculated in g/L): glucose 20.0, yeast powder 10.0, peptone 10.0, dipotassium hydrogen phosphate 1.0, potassium dihydrogen phosphate 0.5, ammonium sulfate 2.0, magnesium sulfate 0.1, and a cosubstrate 5.0, as well as a trace element nutrient solution 0.15-1.0 (mL/L). The cosubstrate is one or both of acetate and butyrate.

The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5-6.0, and the medium was sterilized at 115° C. for 30 min.

(2) Preparation of an *Oscillospiraceae* sp. LBM10036 Bacterial Solution

The medium prepared in step 1 was inoculated with the *Oscillospiraceae* sp. LBM10036 preserved at −80° C. and was activated for cultivation at 37° C. until the OD600 was 1.5-2.0, then transferred to a fresh medium prepared in step 1 at an inoculum concentration of 5% (v/v) and cultivated for 12-18 h, and then transferred to 2 bottles of 500 mL fermentation medium containing glucose as a carbon source at an inoculum concentration of 5% (v/v) for conducting anaerobic standing fermentation at 37° C. for 48 h for use.

(3) Preparation of a Solid-State Fermentation System

Sorghum was crushed to an appropriate size and soaked for 30 min, rice husks were steamed for 30 min, and the soaked sorghum was mixed evenly with the steamed rice husks, steamed for 60 min, and then spread to cool to room temperature. After spreading and cooling, koji powder was added and mixed evenly, and the mass ratio of the sorghum to the rice husks to the koji powder was 4:1:1. The solid fermentation substrate was divided in 7 glass jars (1.4 L), placed in a room with a relatively constant temperature, sealed and fermented for 2 weeks. After 2 weeks, the ethanol contents were detected. After it was confirmed that the fermentation was normal, 200 mL of the *Oscillospiraceae* sp. LBM10036 bacterial solution prepared in step (2) by 48 h of fermentation was added to experimental groups, the same volume of medium was added to control groups, and sealed fermentation was continued for 4 weeks. After the fermentation, 100 g of fermented grains were taken from each group and distilled, and the distillates were treated to detect the concentrations of 3 esters, namely ethyl caproate, ethyl acetate, and ethyl lactate, by gas chromatography (as shown in Table 10).

TABLE 10

Comparison in ester production between the *Oscillospiraceae* sp. LBM10036 simulated fermentation experimental group and the control group

| Concentration (mg/L) | Experimental group 1 | Experimental group 2 | Experimental group 3 | Control group 1 | Control group 2 | Control group 3 |
|---|---|---|---|---|---|---|
| Ethyl caproate | 764 | 136 | 149 | 0 | 0 | 0 |
| Ethyl acetate | 107 | 63 | 732 | 191 | 195 | 477 |
| Ethyl lactate | 227 | 186 | 46 | 991 | 997 | 652 |

After detection, the experimental groups have a relatively high content of ethyl caproate (136-764 mg/L, with an average of 350±358.9 mg/L), while no ethyl caproate is detected from the control groups, indicating that the added *Oscillospiraceae* sp. LBM10036 bacterial solution effectively and significantly promotes the synthesis of ethyl caproate in the fermentation system.

The contents of ethyl lactate in the experimental groups (46-227 mg/L, with an average of 153±94.9 mg/L) is significantly reduced compared to the control groups (652-991 mg/L, with an average of 880±197.5 mg/L), indicating that the addition of the *Oscillospiraceae* sp. LBM10036 utilizes lactic acid generated during fermentation for growth and synthesis of caproic acid, and it is also possible that the addition of the *Oscillospiraceae* sp. LBM10036 inhibits the growth of lactic acid bacteria.

The simulated fermentation shows that the *Oscillospiraceae* sp. LBM10036 can increase the content of ethyl caproate in a Baijiu fermentation system, and have an effect of increasing ethyl caproate and reducing ethyl lactate.

Example 10: Capability of the *Oscillospiraceae* sp. LBM10036 to Tolerate Toxicity of Caproic Acid A brewing environment of Strong aroma-type Baijiu is characterized by a low pH, and the lower the pH, the higher the content of free caproic acid in a system. Free caproic acid can cause toxicity to bacterial cells, therefore, the stronger the tolerance of bacterial cells to the toxicity of caproic acid, the more favorable it is for the survival of the bacterial cells in a system. The growth of the *Oscillospiraceae* sp. LBM10036 was tracked and measured by designing liquid mediums with different initial concentrations of caproic acid.

Specific steps are as follows:
1. Preparation of a Medium
(1) The Used Medium is an Modified *Clostridium* Growth Medium.

The medium contains (calculated in g/L): glucose 20.0, yeast powder 10.0, peptone 10.0, dipotassium hydrogen phosphate 1.0, potassium dihydrogen phosphate 0.5, ammonium sulfate 2.0, magnesium sulfate 0.1, and a cosubstrate 5.0, as well as a trace element nutrient solution 0.15-1.0 (mL/L). The cosubstrate is one or both of acetate and butyrate. The trace element nutrient solution contains (calculated in g/L): calcium chloride 10, cobalt chloride 10, zinc sulfate 10, manganese sulfate 10, and ferrous sulfate heptahydrate 15. The pH of the medium is 5.5, and the medium was sterilized at 115° C. for 30 min.

(2) Preparation of Mediums with Different Concentrations of Caproic Acid

The dissolved medium was divided into 5 blue cap bottles (100 mL), each blue cap bottle containing 100 mL of medium. Before sterilization, the initial concentrations of caproic acid in the mediums were adjusted to 0 g/L, 1 g/L, 2 g/L, 3 g/L, and 4 g/L using a caproic acid standard. At this point, the initial concentrations of free caproic acid in the mediums were 0 g/L, 0.19 g/L, 0.37 g/L, 0.56 g/L, and 0.75 g/L, respectively. The mediums were sterilized at 115° C. for 30 min. After sterilization, the medium of each initial concentration gradient of caproic acid was divided into 3 parts, each part containing 30 mL in a 50 mL centrifuge tube. The residual mediums were taken out of an anaerobic incubator for re-determining the pH and initial concentrations of total caproic acid, and calculating whether the actual concentrations of free caproic acid meet the experimental design.

2. Inoculation of the Mediums with the *Oscillospiraceae* sp. LBM10036 Containing Different Concentrations of Free Caproic Acid (1) An *Oscillospiraceae* sp. LBM10036 frozen glycerol tube was taken out from a −80° C. refrigerator, activated for cultivation for the first generation at 37° C. in the modified *Clostridium* growth medium prepared in (1) step 1 until the OD600 was 1.5-2.0 to obtain a first generation seed solution, and then the first generation seed solution was transferred to a fresh modified *Clostridium* growth medium at an inoculum concentration of 5% (v/v) and activated for the second generation cultivation at 37° C. for 12-18 h until the OD600 was 1.5-2.0 to obtain a second generation seed solution.

(2) 100 mL of the modified *Clostridium* growth medium described in step (1) was inoculated with the second generation seed solution obtained in step (1) at an inoculum concentration of 5% (v/v) and cultivated until the OD value was 1.5-2.0, to obtain a culture solution.

Figure 4:
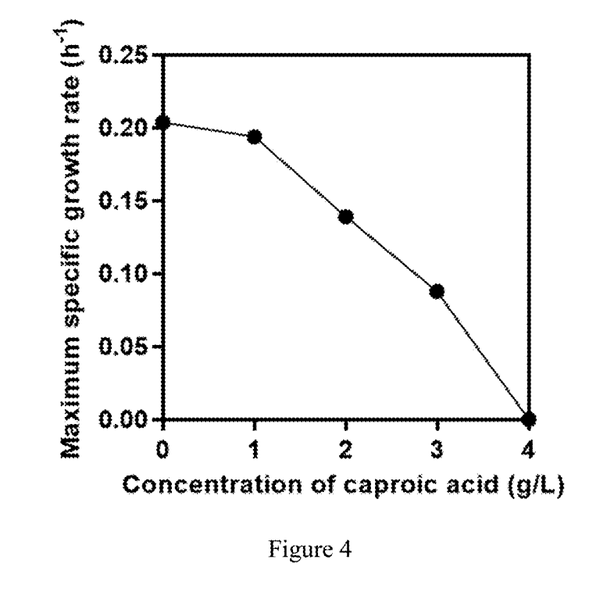
FIG. 4 shows the maximum specific growth rate of the *Oscillospiraceae* sp. LBM10036 at different initial concentration gradients of caproic acid.

(3) The mediums with different initial concentration gradients of caproic acid prepared in (2) of step 1 were inoculated with the prepared culture solution at an inoculum concentration of 5% (v/v). The medium of each initial concentration gradient of caproic acid had 3 replicates, and sampled from 0 to 72 h at an interval of 12 h. The OD600 was measured using a spectrophotometer, and the results are shown in Tables 11. The maximum specific growth rates under different initial concentration gradients of caproic acid were plotted (as shown in FIG. 4).

TABLE 11

OD600 values of *Oscillospiraceae* sp. under different initial concentration gradients of caproic acid

| Time | 0 g/L | 1 g/L | 2 g/L | 3 g/L | 4 g/L |
|---|---|---|---|---|---|
| 0 h | 0.18 ± 0.01 | 0.26 ± 0.00 | 0.27 ± 0.01 | 0.26 ± 0.01 | 0.23 ± 0.01 |
| 12 h | 0.56 ± 0.10 | 0.53 ± 0.02 | 0.30 ± 0.02 | 0.69 ± 0.06 | 0.22 ± 0.01 |
| 24 h | 2.35 ± 0.26 | 1.96 ± 0.17 | 1.06 ± 0.37 | 0.88 ± 0.07 | 0.20 ± 0.01 |
| 48 h | 2.51 ± 0.04 | 2.39 ± 0.20 | 2.00 ± 0.10 | 1.46 ± 0.07 | 0.21 ± 0.04 |
| 72 h | 2.25 ± 0.17 | 2.25 ± 0.32 | 1.72 ± 0.17 | 1.44 ± 0.05 | 0.20 ± 0.02 |

The results indicate that the optimal condition for the growth of the *Oscillospiraceae* sp. LBM10036 is without addition of caproic acid, and the maximum tolerable initial concentration of caproic acid is 3 g/L (concentration of free caproic acid is 0.56 g/L). When an environment contains caproic acid with a concentration of 4 g/L (concentration of free caproic acid is 0.75 g/L), the growth of *Oscillospiraceae* sp. will be significantly inhibited. Due to the fact that the concentration of total caproic acid in pit mud is usually lower than 2 g/L and the pH of pit mud tends to be neutral to alkaline, the *Oscillospiraceae* sp. LBM10036 can adapt well to a pit mud environment and has broad application prospects.

Although the disclosure has been disclosed as above in preferred examples, it is not intended to limit the disclosure. Anyone familiar with the art can make various changes and modifications without departing from the spirit and scope of the disclosure. Therefore, the protection scope of the disclosure should be defined by the claims.

What is claimed is:

1. A method for producing caproic acid, wherein the caproic acid is produced by fermentation of the *Oscillospiraceae* sp. LBM10036, and the *Oscillospiraceae* sp. LBM10036 was preserved in the Guangdong Microbial Culture Collection Center on Sep. 21, 2020, with the preservation number GDMCC No. 61202.

2. The method according to claim 1, wherein the *Oscillospiraceae* sp. LBM10036 utilizes one or more of glucose, fructose, maltose, starch, and lactic acid as carbon sources.

3. The method according to claim 1, wherein the fermentation further comprises utilizing acetate or butyrate as a cosubstrate.

4. The method according to claim 3, wherein the fermentation is conducted at a temperature of 35-37° C. for 3-4 days, at an initial pH of fermentation of 5.5-6.5.

5. The method according to claim 2, wherein one of the carbon sources is 10-40 g/L glucose.

6. The method according to claim 2, wherein one of the carbon sources is 10-40 g/L fructose.

7. The method according to claim 2, wherein one of the carbon sources is 10-40 g/L maltose.

8. The method according to claim 2, wherein one of the carbon sources is 10-40 g/L starch.

9. The method according to claim 2, wherein one of the carbon sources is 10-40 g/L lactic acid.

\* \* \* \* \*